US00PP16568P3

(12) United States Plant Patent
Miyazaki

(10) Patent No.: US PP16,568 P3
(45) Date of Patent: May 23, 2006

(54) ***SENECIO* PLANT NAMED 'SUNSENERAPI'**

(50) Latin Name: ***Senecio cruentus*×*Senecio heritieri***
Varietal Denomination: Sunsenerapi

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 248 days.

(21) Appl. No.: 10/611,355

(22) Filed: Jun. 30, 2003

(65) Prior Publication Data

US 2004/0268454 P1 Dec. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,104 P2 9/2001 Miyazaki
PP12,122 P2 10/2001 Miyazaki
PP12,162 P2 10/2001 Miyazaki
PP12,181 P2 10/2001 Miyazaki

FOREIGN PATENT DOCUMENTS

JP PBR 10653 8/2000
JP PBR 10653 9/2002

OTHER PUBLICATIONS

U.S. Appl. No. 10/611,353, Miyazaki.

*Primary Examiner*—Kent Bell
(74) *Attorney, Agent, or Firm*—Christie, Parker & Hale, LLP

(57) ABSTRACT

Disclosed herein is a *Senecio* plant named 'Sunsenerapi' being of a high height and dome-shaped plant with abundant branching. There are moderate pubescences on its stem. Petiole length is longer than in *Senecio* L. It has a large flower cluster. Capitula are single flowered and have no marginal variegation. The color of the ray floret is light purplish pink and the disk florets are strong reddish purple. Blooming term is longer than *Senecio cruentus*. Flower buds grow one after another from axil.

2 Drawing Sheets

Botanical/commercial classification: *Senecio cruentus*× *Senecio heritieri/Senecio* Plant.
Varietal denomination: cv. 'Sunsenerapi'.

BACKGROUND OF THE VARIETY

The present invention relates to a new and distinct variety of *Senecio* plant named 'Sunsenerapi'. 'Sunsenerapi' is a distinct and unique variety, which is a dome-shaped plant with abundant branching, light purplish pink flowers, and a long blooming term.

There are many varieties of *Senecio* L. cultivated in the world. There are many cultivated varieties with flowers of a single color of white, pink, red, blue or violet. Some varieties have marginal variegation with off color parts.

The female parent used in the crossing to produce 'Sunsenerapi' is a clone of our own breeding line, *Senecio cruentus,* '8S-84e' (not patented in the United States), which is a compact, dome-shaped plant, 16 cm in height. The stems are thick, 8.0 mm in diameter, with no anthocyanin coloration. The leaf is in a serrated heart form and moderate yellow green. The leaf size is medium, approximately 12.0 cm long and approximately 12.5 cm wide. The capitulum is single flowered and has white ray florets with white disk florets having no marginal variegation. '8S-84e' has some scent.

The pollen parent used in the crossing to produce 'Sunsenerapi' is our breeding line (unnamed plant), *Senecio heritieri* (not patented or sold in the United States), which was originally introduced from England. *Senecio heritieri* is a high and dome-shaped plant, approximately 26 cm in height with abundant branching. Stems are approximately 5.1 mm in diameter, with no anthocyanin coloration. The leaf is in a serrated heart form and light yellowish green. The leaf size is small, approximately 5.5 cm long, approximately 6.3 cm wide. The capitulum is single flowered, having strong purple ray florets with vague white parts and strong reddish purple disk florets. *Senecio heritieri* has no scent.

The controlled crossing with a plant of *Senecio cruentus* '8S-84e' and an unnamed plant of *Senecio heritieri* was conducted at Omori-cho, Yokaichi-shi, Shiga, Japan in February, 1999. Seedlings from this crossing were grown since September, 1999. Four strains were selected in January 2000 among them in view of flower color are earliness. After multiplication by tissue culture, the botanical characteristics of the selected new strains were tested in pots since September 2000, using parent varieties and 'Sunsenere' (U.S. Plant Pat. No. 12,162,) and 'Midget' (not patented in the United States) for comparison, since 2000. As a result, one strain was selected. It is confirmed that the instant plant reproduces true to type in successive generations of asexual reproduction.

This new variety of *Senecio* plant was named 'Sunsenerapi' (*Senecio cruentus*×*Senecio heritieri*).

The new variety of *Senecio* plant was asexually reproduced by cuttings at Omori-cho, Yokaichi-shi, Shiga-ken, Japan.

*Senecio cruentus,* '8S-84e', and the unnamed plant of *Senecio heritieri* are presently maintained at Omori-cho, Yokaichi-shi, Shiga-ken, Japan.

In the following descriptions, the color-coding is in accordance with the Horticultural Colour Chart of The Royal Horticultural Society, London, England (R.H.S. Colour Chart).

The botanical characteristics of the female parent plant *Senecio cruentus,* '8S-84e', used in the crossing to produce 'Sunsenerapi' are as follows.

Plant:
*Growth habit.*—Dwarf compact.
*Height.*—Approximately 16 cm.
Stem:
*Thickness.*—Approximately 8.0 mm.
*Color.*—Moderate yellowish green (near R.H.S. No. 139C).
*Anthocyanin coloration.*—Absent.
*Branching.*—Fair.
*Pubescence.*—Sparse.
*Internode length at the middle of main stem.*—Approximately 0.5 cm.
Leaf:
*Whole shape.*—Heart form with a swollen basal part, which is notched where the basal part of the blade attaches to the petiole.
*Depth of concavity of leaf margin.*—Medium.
*Type of convexity.*—Acute.
*Apex shape.*—Obtuse.
*Base shape.*—Cordate.
*Degree of undulation.*—Fair.
*Length.*—Approximately 12.0 cm.
*Width.*—Approximately 12.5 cm.
*Diameter of petiole.*—Approximately 5.0 mm.
*Length of petiole.*—Approximately 5.5 cm.
*Color of upper surface.*—Moderate yellow green (near R.H.S. No.137C).
*Color of reverse surface.*—Grayish yellow green (near R.H.S. No.138B).
*Anthocyanin coloration of reverse surface.*—Absent.
*Pubescence of upper surface.*—Present.
*Pubescence of reverse surface.*—Dense.
*Color of pubescence of reverse surface.*—White.
Flower cluster (gathering of corymbs):
*Shape of flower cluster.*—Flat.
*Diameter of flower cluster.*—Approximately 20 cm.
*Height of flower cluster.*—Approximately 8 cm.
Capitula:
*Transected shape of capitula.*—Flat.
*Diameter of capitula.*—Approximately 5.5 cm.
*Diameter of disk entire capitula.*—Approximately 1.2 cm.
*Color of ray floret.*—White (near R.H.S. No.155D).
*Marginal variegation.*—Absent.
*Color of disk floret.*—White (near R.H.S. No.155D).
*Ray floret length.*—Approximately 2.1 cm.
*Ray floret width.*—Approximately 1.0 cm.
*Shape of ray floret.*—Elliptical.
*Lengthwise warp of ray floret.*—Flat.
*Concavity of ray floret tip.*—Present.
*Shape of ray floret tip.*—Rounded.
*Number of ray floret.*—Approximately 13.
*Number of disk floret.*—Approximately 105.
*Diameter of pedicel of the first capitulum.*—Approximately 1.6 mm.
*Length of pedicel of the first capitulum.*—Approximately 2.4 cm.
*Number of capitula per plant.*—Approximately 75.
*Scent.*—Present.
Phyllaries:
*Length.*—Approximately 2.2 mm.
*Color.*—Moderate yellow green (near R.H.S. No.139C).
*Anthocyanin coloration.*—Absent.
Pistil:
*Color.*—Light yellow (near R.H.S. No.11B).
*Number.*—1.
*Type.*—Style branches truncate (i.e., the top of the style is separated in two and the shape of the top is truncated).
Stamen:
*Color.*—Brilliant yellow (near R.H.S. No.12B).
*Type.*—5 anthers are connate, with separated filaments.
Blooming period — January (sowing in August):
Hardiness:
*Cold.*—Good.
*Rain.*—Good.
*Heat.*—Good.
Resistance:
*Disease.*—Good.
*Insect.*—Good.

The botanical characteristics of the male parent plant *Senecio heritieri* used in the crossing to produce 'Sunsenerapi' are as follows.

Plant:
*Growth habit.*—Dwarf compact.
*Height.*—Approximately 26 cm.
Stem:
*Thickness.*—Approximately 5.1 mm.
*Color.*—Very pale green (near R.H.S. No.128D).
*Anthocyanin coloration.*—Absent.
*Branching.*—Abundant.
*Type of primary lateral shoot.*—Branch from every node.
*Pubescence.*—Dense.
*Internode length at the middle of main stem.*—Approximately 0.8 cm.
Leaf:
*Whole shape.*—Heart form with a swollen basal part, which is notched where the basal part of the blade attaches to the petiole.
*Depth of concavity of leaf margin.*—Medium.
*Type of convexity.*—Acute.
*Apex shape.*—Obtuse.
*Base shape.*—Cordate.
*Degree of undulation.*—Weak.
*Length.*—Approximately 5.5 cm.
*Width.*—Approximately 6.3 cm.
*Diameter of petiole.*—Approximately 4.2 mm.
*Length of petiole.*—Approximately 7.5 cm.
*Color of upper surface.*—Light yellowish green (near R.H.S. No.136D).
*Color of reverse surface.*—Very pale green (near R.H.S. No.128D).
*Anthocyanin coloration of reverse surface.*—Absent.
*Pubescence of upper surface.*—Dense.
*Pubescence of reverse surface.*—Dense.
*Color of pubescence of reverse surface.*—White.
Flower cluster (gathering of corymbs):
*Shape of flower cluster.*—Uneven.
*Diameter of flower cluster.*—Approximately 18 cm.
*Height of flower cluster.*—Approximately 15 cm.

Capitula:
*Transected shape of capitula.*—Flat.
*Diameter of capitula.*—Approximately 4.8 cm.
*Diameter of entire disk.*—Approximately 0.9 cm.
*Color of ray floret.*—Strong purple (near R.H.S. No.81B).
*Marginal variegation.*—Present.
*Diameter of off color part.*—Approximately 1.3 cm.
*Border of marginal variegation.*—Vague.
*Color of disk floret.*—Strong reddish purple (near R.H.S. No.72A).
*Ray floret length.*—Approximately 2.2 cm.
*Ray floret width.*—Approximately 0.4 cm.
*Shape of ray floret.*—Rectangular.
*Lengthwise warp of ray floret.*—Flat.
*Concavity of ray floret tip.*—Present.
*Shape of ray floret tip.*—Acute.
*Number of ray floret.*—Approximately 13.
*Number of disk floret.*—Approximately 110.
*Diameter of pedicel of the capitulum.*—Approximately 1.2 mm.
*Length of pedicel of the capitulum.*—Approximately 2.5 cm.
*Number of capitula per plant.*—Approximately 35.
*Scent.*—Absent.
Phyllaries:
*Length.*—Approximately 3.1 mm.
*Color.*—Very pale green (near R.H.S. No.128D).
*Anthocyanin coloration.*—Present.
Pistil:
*Color.*—Strong reddish purple (near R.H.S. No.72A).
*Number.*—1.
*Type.*—Style branches truncate (i.e., the top of the style is separated in two and the shape of the top is truncated).
Stamen:
*Color.*—Strong reddish purple (near R.H.S. No.72A).
*Type.*—5 anthers are connate, with separated filaments.
Blooming period — End of January (sowing in August).
Hardiness:
*Cold.*—Good.
*Rain.*—Good.
*Heat.*—Good.
Resistance:
*Disease.*—Good.
*Insect.*—Good.

The botanical characteristics of a similar variety 'Sunsenere' (*Senecio cruentus*×*Senecio heritieri*) which was patented in the United States, used for examination as a comparison variety are as follows.

Plant:
*Growth habit.*—Semi-dwarf erect.
*Height.*—Approximately 25 cm.
Stem:
*Thickness.*—Approximately 5.0 mm.
*Color.*—Moderate yellowish green (near R.H.S. No.139C).
*Anthcyanin coloration.*—Present in parts of stem, e.g., can be seen at the part of peduncle.
*Degree of anthocyanin coloration.*—It is light grayish olive (near R.H.S. No.197A) at the part wherein anthocyanin is present, but it is moderate yellowish green (near R.H.S. No.138C) at the part where anthocyanin is absent.
*Branching.*—Abundant, i.e., approximately 9 to 11 branches.
*Type of primary lateral shoot.*—Branch from every node.
*Pubescence.*—Sparse.
*Internode length at the middle of main stem.*—Approximately 1.0 cm.
Leaf:
*Whole shape.*—Heart form with a swollen basal part, which is notched where the basal part of the blade attaches to the petiole.
*Depth of concavity of leaf margin.*—The maximum depth of concavity measured from the average convexity peak height is approximately 7 mm.
*Type of convexity.*—Acute.
*Apex shape.*—Obtuse.
*Base shape.*—Cordate.
*Degree of undulation.*—Weak.
*Length.*—Approximately 8.6 cm.
*Width.*—Approximately 10.3 cm.
*Diameter of petiole.*—Approximately 3.2 mm.
*Length of petiole.*—Approximately 9.0 cm.
*Color of upper surface.*—Moderate yellow green (near R.H.S. No.137C).
*Color of reverse surface.*—Moderate yellow green (near R.H.S. No.138C).
*Anthocyanin coloration of reverse surface.*—Absent.
*Pubescence of upper surface.*—Dense.
*Pubescence of reverse surface.*—Dense.
*Color of pubescence of reverse surface.*—White.
Flower cluster (gathering of corymbs):
*Shape of flower cluster.*—Uneven.
*Diameter of flower cluster.*—Approximately 34 cm.
*Height of flower cluster.*—Approximately 22 cm.
Capitula:
*Transected shape of capitula.*—Flat.
*Diameter of capitula.*—Approximately 6.4 cm.
*Diameter of entire disk.*—Approximately 1.3 cm.
*Color of ray floret.*—Vivid reddish purple (near R.H.S. No.78A).
*Marginal variegation.*—Absent.
*Color of disk floret.*—Deep reddish purple (near R.H.S. No.80A).
*Ray floret length.*—Approximately 2.6 cm.
*Ray floret width.*—Approximately 0.8 cm.
*Shape of ray floret.*—Rectangular.
*Lengthwise warp of ray floret.*—Flat.
*Concavity of ray floret tip.*—Present.
*Shape of ray floret tip.*—Acute.
*Number of ray floret.*—Approximately 15–16.
*Number of disk floret.*—Approximately 130.
*Diameter of pedicel of the first capitulum.*—Approximately 1.2 mm.
*Length of pedicel of the first capitulum.*—Approximately 3.3 cm.
*Number of capitula per plant.*—Approximately 88.
*Scent.*—Present.
Phyllaries:
*Length.*—Approximately 1.2 mm.
*Color.*—Very pale green (near R.H.S. No.130D).
*Anthocyanin coloration.*—Absent.
Pistil:
*Color.*—Vivid reddish purple (near R.H.S. No.80A).
*Number.*—1.
*Type.*—Style branches truncate (i.e., the top of the style is separated in two and the shape of the top is truncated).

Stamen:
*Color.*—Vivid reddish purple (near R.H.S. No.80A).
*Type.*—5 anthers are connate, with separated filaments.
*Blooming period.*—Start at the end of November or early December (cutting in July).
Hardiness:
*Cold.*—Good.
*Rain.*—Good.
*Heat.*—Good.
Resistance:
*Disease.*—Good.
*Insect.*—Good.

The botanical characteristics of a similar variety 'Midget', used for examination as a comparison variety are as follows.

Plant:
*Growth habit.*—Dwarf.
*Height.*—Approximately 14 cm.
Stem:
*Thickness.*—Approximately 5.6 mm.
*Color.*—Moderate yellow green (near R.H.S. No. 139C).
*Anthocyanin coloration.*—Present.
*Degree of anthocyanin coloration.*—Medium.
*Branching.*—Fair.
*Pubescence.*—Dense.
*Internode length at the middle of main stem.*—Approximately 0.5 cm.
Leaf:
*Whole shape.*—Heart form with a swollen basal part, which is notched at where the basal part of the blade attaches to the petiole.
*Depth of concavity of leaf margin.*—Medium.
*Type of convexity.*—Acute.
*Apex shape.*—Acute.
*Base shape.*—Cordate.
*Degree of undulation.*—Fair.
*Length.*—Approximately 13.9 cm.
*Width.*—Approximately 10.3 cm.
*Diameter of petiole.*—Approximately 4.2 mm.
*Length of petiole.*—Approximately 4.7 cm.
*Color of upper surface.*—Grayish yellow green (near R.H.S. No.138A).
*Color of reverse surface.*—Grayish yellow green (near R.H.S. No.138B).
*Anthocyanin coloration of reverse surface.*—Absent.
*Pubescence of upper surface.*—Present.
*Pubescence of reverse surface.*—Dense.
*Color of pubescence of reverse surface.*—White.
Flower cluster (gathering corymbs):
*Shape of flower cluster.*—Flat.
*Diameter of flower cluster.*—Approximately 22 cm.
*Height of flower cluster.*—Approximately 8 cm.
Capitula:
*Transected shape of capitula.*—Fairly closed.
*Diameter of capitula.*—Approximately 3.2 cm.
*Diameter of entire disk.*—Approximately 0.8 cm.
*Color or ray floret.*—Vivid reddish purple (near R.H.S. No.74A).
*Marginal variegation.*—Absent.
*Color of disk floret.*—Strong reddish purple (near R.H.S. No.72A).
*Ray floret length.*—Approximately 1.5 cm.
*Ray floret width.*—Approximately 0.8 cm.
*Shape of ray floret.*—Elliptical.
*Lengthwise warp of ray floret.*—Flat.
*Concavity of ray floret tip.*—Present.
*Shape of ray floret tip.*—Acute.
*Number of ray floret.*—Approximately 13.
*Number of disk floret.*—Approximately 86.
*Diameter of pedicel of the first capitulum.*—Approximately 1.5 mm.
*Length of pedicel of the first capitulum.*—Approximately 2.5 cm.
*Number of capitula per plant.*—Approximately 180.
*Scent.*—Present.
Phyllaries:
*Length.*—Approximately 2.2 mm.
*Color.*—Moderate yellow green (near R.H.S. No.139C).
*Anthocyanin coloration.*—Absent.
Pistil:
*Color.*—Strong reddish purple (near R.H.S. No.72A).
*Number.*—1.
*Type.*—Style branches truncate (i.e., the top of the style is separated in two and the shape of the top is truncated).
Stamen:
*Color.*—Strong reddish purple (near R.H.S. No.72A).
*Type.*—5 anthers are connate, with separated filaments.
Blooming period — January (sowing in August):
Hardiness:
*Cold.*—Good.
*Rain.*—Good.
*Heat.*—Good.
Resistance:
*Disease.*—Good.
*Insect.*—Good.

SUMMARY OF THE NEW VARIETY

'Sunsenerapi' is a dome-shaped plant with an average height of approximately 31.8 cm in the blooming period. There is a branch from every node and branching is abundant, i.e., approximately 9 to 11 branches. The stem is approximately 4.8 mm in diameter with light pubescence.

The leaves are small, approximately 13.9 cm long, approximately 9.7 cm wide. The leaves are shaped in a serrated heart form with a swollen basal part, which is notched where the basal part of the blade attaches to the petiole. The leaf color is moderate olive green, with no anthocyanin coloration on the reverse side. Pubescence on both sides of leaf is dense. The petiole is approximately 10.0 cm long and approximately 3.4 mm in diameter.

The new variety has large flower clusters which are high and uneven in shape (i.e., the locations of the individual capitula forming the cluster are uneven or not flat). A flower cluster means a gathering of capitula in a plant. The capitulum is single flowered with no marginal variegation. The capitulum has a flat transected shape (i.e., when the capitulum opens, ray florets are flat when viewed from the side). The capitula is approximately 6.7 cm in diameter, while the entire disk is approximately 1.3 cm in diameter. The ray florets are approximately 3.1 cm long and approximately 0.8 cm wide. The color of the ray floret is light purplish pink (near R.H.S. No.75C), while the color of the disk florets are strong reddish purple (near R.H.S. No.77B). One capitulum has approximately 13 ray florets and approximately 167 disk florets. A ray floret has a pistil, but no stamen. A disk floret is tubular and has a pistil and a stamen formed by 5 connate anthers with separated filaments. There are approximately 155 capitula per plant. The length of phyllary is approximately 2.0 mm. The phyllary has no anthocyanin coloration. The pedicel is approximately 3.9 cm long and approximately 1.2 mm in diameter. The flowers have some scent.

After cutting in July, the plant flowers at the end of the January in Japan. The blooming continues from January to May, if under appropriate control. By temperatures around 15° C., the individual bloom lasts two weeks. The flower buds grow one after another from the axil. The flower is not self-cleaning because florets remain attached in a wilted and dry state as the flower fully matures.

The new variety has moderate cold and heat tolerance. The new variety does not die at around 0° C., but when frost occurs the cells can be necrosed resulting in the death of the plant. Usually, *Senecio cruentus* has a tendency of slightly reduced growth in a hot season, whereas the new variety has no problem in growing in the hot season.

The fertility of the new variety is low. Generally, *Senecio* genus plants have high fertility (i.e., bear many seeds per flower). In contrast, 'Sunsenerapi' bears no seed or very few seeds per capitulum. When no seed is formed, there is a part corresponding to a seed coat, which remains in an immature state, i.e., without embryo and endosperm inside the immature seed coat.

The new variety, 'Sunsenerapi', differs from similar varieties, 'Sunsenere' and 'Midget', of the *Senecio* genus and from parent varieties, the unnamed plant of *Senecio heritieri* and '8S-84e' in the following points.

1. 'Sunsenerapi' is a high type plant, approximately 31.8 cm in height. 'Sunsenere' is a high type plant, approximately 25 cm in height. 'Midget' is a compact type plant, approximately 14 cm in height. The pollen parent *Senecio heritieri* is a semi-compact type plant, approximately 26 cm in height and female plant '8S-84e' is a compact type plant, approximately 16 cm in height.
2. The capitulum of 'Sunsenerapi' has light purplish pink ray florets, strong reddish purple disk florets and no marginal variegation, while 'Sunsenere' has vivid reddish purple ray florets, deep reddish purple disk florets and no marginal variegation. 'Midget' has vivid reddish purple ray florets, strong reddish purple disk florets and no marginal variegation. The female parent, '8S-84e' has white ray florets, white disk florets and no marginal variegation. The pollen parent *Senecio heritieri* has strong purple ray florets, strong reddish purple disk florets and white marginal part.
3. The petiole length of 'Sunsenerapi' is longer than that of 'Sunsenere' or 'Midget'.
4. 'Sunsenerapi' has more pubescence of stems than 'Sunsenere' and fewer than 'Midget'.
5. The blooming term of 'Sunsenerapi' is longer than 'Midget'.
6. The fertility of 'Sunsenerapi' is lower than 'Midget'.

The plant height and flower color are most distinctive characteristics of this new variety, 'Sunsenerapi'.

DESCRIPTION OF THE NEW VARIETY

Figure 1:
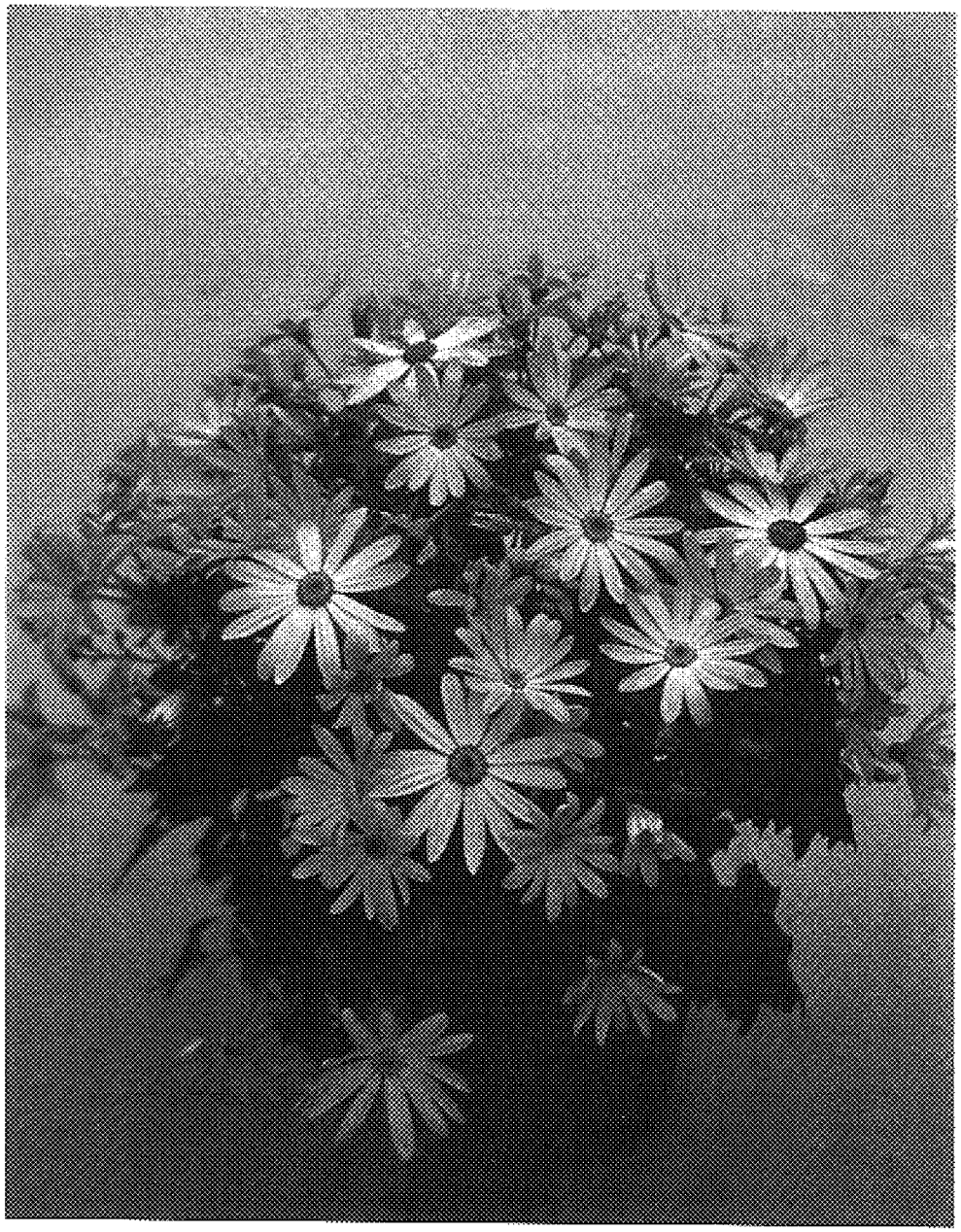
FIG. 1 is a photograph giving a partial view of the new variety of *Senecio* plant named 'Sunsenerapi' planted in a pot.
Figure 2:
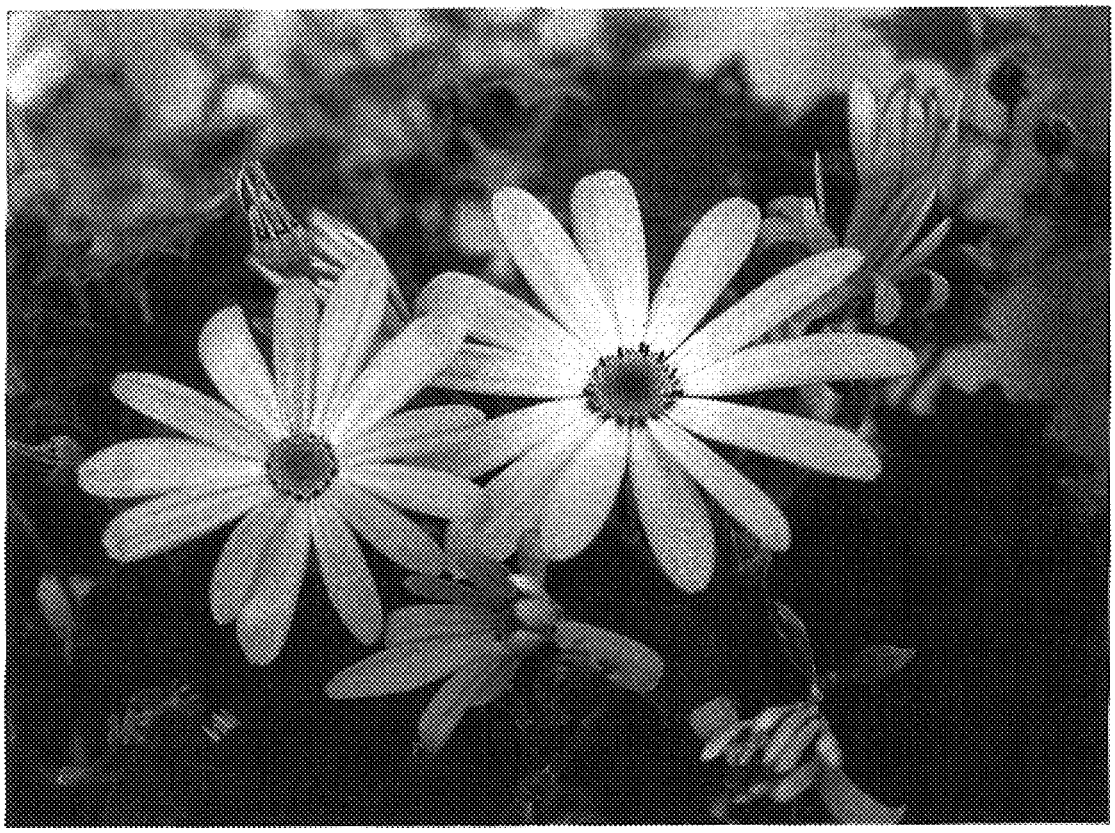
FIG. 2 is a photograph of capitula of the new variety of *Senecio* plant named 'Sunsenerapi'.

The botanical characteristics of this new and distinct variety of *Senecio* plant named 'Sunsenerapi' at an age of 7 months after cutting in July at Omori-cho, Yokaichi-shi, Shiga-ken, Japan are as follows (i.e., these botanical characteristics were observed in January of the year following the cutting with the new variety planted in a 15 cm pot and grown in a greenhouse, the lowest temperature of which was controlled at 12° C. in winter).

Plant:
- *Growth habit.*—Semi-dwarf erect.
- *Height.*—Approximately 31.8 cm.
- *Spread.*—Approximately 35 cm.

Stem:
- *Lateral stem length.*—Approximately 12.0 cm.
- *Lateral stem diameter.*—Approximately 3.5 mm.
- *Color.*—Very pale green (near R.H.S. No.130D).
- *Anthocyanin coloration.*—Absent.
- *Branching.*—Abundant, i.e., approximately 9 to 11 branches.
- *Type of primary lateral shoot.*—Branch from every node.
- *Pubescence.*—Medium.
- *Internode length at the middle of the main stem.*—Approximately 1.8 cm.

Leaf:
- *Whole shape.*—Heart form with a swollen basal part, which is notched where the basal part of the blade attaches to the petiole.
- *Depth of concavity of leaf margin.*—The maximum depth of concavity measured from the average convexity peak height is approximately 5 mm.
- *Type of convexity.*—Acute.
- *Apex shape.*—Acute.
- *Base shape.*—Cordate.
- *Margin.*—Palmately lobed, crenate and weakly undulated.
- *Length.*—Approximately 13.9 cm.
- *Width.*—Approximately 9.7 cm.
- *Diameter of petiole.*—Approximately 3.4 mm.
- *Length of petiole.*—Approximately 10.0 cm.
- *Petiole color.*—Near R.H.S. 145B.
- *Color of upper surface.*—Moderate olive green (near R.H.S. No.146A).
- *Color of reverse surface.*—Moderate yellow green (near R.H.S. No.147D).
- *Anthocyanin coloration of reverse surface.*—Absent.
- *Pubescence of upper surface.*—Sparse.
- *Pubescence of reverse surface.*—Dense.
- *Color of pubescence of reverse surface.*—White.

Flower cluster (gathering of corymbs):
- *Shape of flower cluster.*—Round.
- *Diameter of flower cluster.*—Approximately 34 cm.
- *Height of flower cluster.*—Approximately 22 cm.

Capitula:
- *Transected shape of capitula.*—Flat.
- *Diameter of capitula.*—Approximately 6.7 cm.
- *Diameter of entire disk.*—Approximately 1.3 cm.
- *Color of ray floret (upper).*—Light purplish pink (near R.H.S. No.75C); color of ray floret (lower) — near R.H.S. 76C.
- *Marginal variegation.*—Absent.
- *Color of disk floret.*—Strong reddish purple (near R.H.S. No.77B).

*Ray floret length.*—Approximately 3.1 cm.
*Ray floret width.*—Approximately 0.8 cm.
*Ray floret margin.*—Entire.
*Base shape of ray floret.*—Obtuse.
*Shape of ray floret.*—Long oblong.
*Lengthwise warp of ray floret.*—Flat.
*Concavity of ray floret tip.*—Present.
*Shape of ray floret tip.*—Acute.
*Number of ray floret.*—Approximately 13.
*Number of disk floret.*—Approximately 167.
*Diameter of pedicel of the first capitulum.*—Approximately 1.2 mm.
*Length of pedicel of the first capitulum.*—Approximately 3.9 cm.
*Color.*—Near R.H.S. 152B.
*Number of capitula per plant.*—Approximately 155.
*Scent.*—Present.

Disk floret:
*Length.*—Approximately 8.5 mm.
*Width.*—Approximately 2.0 mm.
*Shape.*—Tubular trumpet shape.

Phyllaries:
*Number of phillaries.*—Approximately 14.
*Length.*—Approximately 2.0 mm.
*Color.*—Moderate yellow green (near R.H.S. No.139C).
*Anthocyanin coloration.*—Absent.
*Shape.*—Lanceolate.
*Apex.*—Acute.
*Margin.*—Entire.
*Base.*—Fused.

Bud:
*Diameter.*—Approximately 6.0 mm.
*Length.*—Approximately 5.5 mm.
*Shape.*—Globose.
*Color.*—Near R.H.S. 144B.

Pistil:
*Color.*—Vivid purple (near R.H.S. No.82A).
*Number.*—1 per ray and disk floret.
*Type.*—Style branches truncate (i.e., the top of the style is separated in two and the shape of the top is truncated).

Stamen:
*Color.*—Dark yellow (near R.H.S. No.153B).
*Type.*—A disk floret has 5 connate anthers with separated filaments. Ray floret has no stamen.
*Amount of pollen.*—Scarce.
*Pollen color.*—Near R.H.S. 21C.

Blooming period — start at the end of January (cutting in July):
*Time to flower.*—Approximately 6 months.

Hardiness:
*Cold.*—Good.
*Rain.*—Good.
*Heat.*—Good.

Resistance:
*Disease.*—Good.
*Insect.*—Good.

The new variety and *Senecio cruentus* have similar resistance to powdery mildew, leaf spot, aphid, whitefly, and thrips. The new variety, 'Sunsenerapi', is a tall type plant and most suitable for flower potting.

This new and distinct variety of *Senecio* plant named 'Sunsenerapi' was asexually reproduced by cutting at Omori-cho, Yokaichi-shi, Shiga-ken, Japan and the homegeneity and stability thereof were confirmed.

It is claimed:

1. A new and distinct variety of *Senecio* plant named 'Sunsenerapi', substantially as herein illustrated and described.

* * * * *